United States Patent [19]
Li et al.

[11] Patent Number: 5,324,328
[45] Date of Patent: Jun. 28, 1994

[54] CONDUCTOR FOR A DEFIBRILLATOR PATCH LEAD

[75] Inventors: Hong Li, Irvine; Phong D. Doan, Stevenson Ranch; John R. Helland, Saugus, all of Calif.

[73] Assignee: Siemens Pacesetter, Inc., Sylmar, Calif.

[21] Appl. No.: 926,075

[22] Filed: Aug. 5, 1992

[51] Int. Cl.$^5$ .............................................. A61N 1/05
[52] U.S. Cl. ..................................................... 607/129
[58] Field of Search ........... 128/784, 785, 798, 419 D, 128/642, 639–642/; 607/5, 115, 116, 129, 130, 131, 132

[56] References Cited

U.S. PATENT DOCUMENTS

| | | | |
|---|---|---|---|
| 1,212,541 | 1/1916 | Morse | 128/798 |
| 2,536,271 | 1/1951 | Fransen | 128/798 |
| 4,314,095 | 2/1982 | Moore et al. | 174/84 C |
| 4,411,277 | 10/1983 | Dickhudt | 128/784 |
| 4,827,932 | 5/1989 | Ideker et al. | 128/784 X |
| 5,042,463 | 8/1991 | Lekholm | 128/642 X |

OTHER PUBLICATIONS

Timmis, Gerald C., "The Electrobiology and Engineering of Pacemaker Leads," Chapter 4, pp. 35–90, Section—Electrical Therapy for Bradyarrhythmias, *Electrical Therapy for Cardiac Arrhythmias* (W. B. Saunders Company—1990).

*Primary Examiner*—Lee S. Cohen
*Assistant Examiner*—Jeffrey R. Jastrzab
*Attorney, Agent, or Firm*—Lisa P. Weinberg; Malcolm J. Romano

[57] ABSTRACT

An electrical conductor assembly utilized, for example, in a defibrillator patch lead to interconnect a pulse generator and monitoring unit, and a wire mesh electrode pad. The electrical conductor includes a Teflon insulated drawn brazed stranded (DBS) wire cable which is wrapped in a drawn filled tube (DFT) wire multifilar coil encased in a biocompatible insulative tubing.

10 Claims, 2 Drawing Sheets

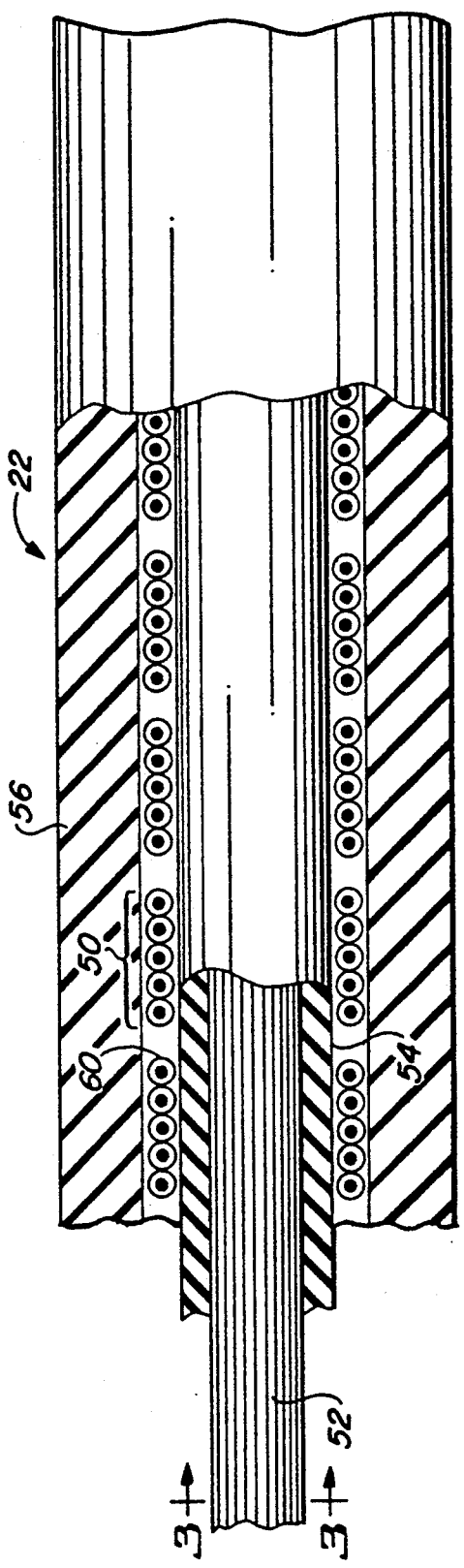
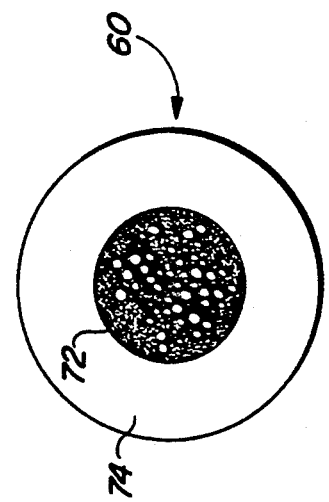
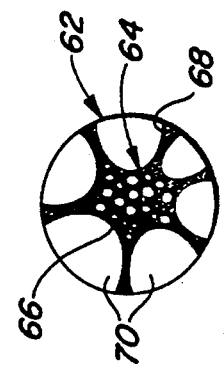
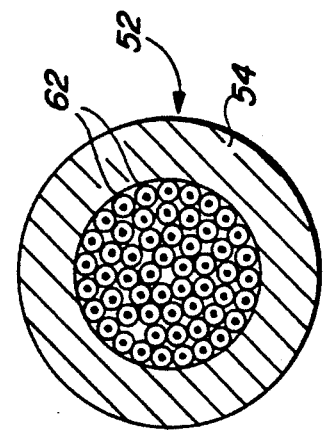

CONDUCTOR FOR A DEFIBRILLATOR PATCH LEAD

FIELD OF THE INVENTION

The present invention relates to the field of implantable medical devices for sensing and manipulating cardiac activity. More specifically, the present invention details an improved conductor for an implantable defibrillator lead with a patch electrode adapted to be affixed to the exterior surface of the heart and connected to a signal processing and power generating unit.

BACKGROUND OF THE INVENTION

The continuing evolution in the medical field of the study and control of cardiac activity requires advances in the designs of various implantable devices utilized to control cardiac activity. Various types of implantable leads utilize electrodes, which are currently either implanted into an interior chamber of the heart or which are affixed to the exterior surface of the heart, or within or upon the pericardial sac which surrounds the heart. These devices, depending upon their intended implant location, have various specific requirements. For the devices designed to be affixed to the exterior surface of the heart, or implanted within or upon the pericardial sac, the environment places specific design constraints on the materials and construction of the devices.

For patch electrodes which are affixed to the external surface of the heart, or within or on the pericardial sac, the environment requires that the electrode be highly resistant to fractures caused by the flexing resulting from the continuous beating of the heart. In addition, the electrodes must exhibit high conductivity, high flexibility, and biological inertness. For various types of cardiac electrodes, the use of very fine titanium or platinum wire mesh, which provides very good electrical properties while being able to conform to the shape of the heart, has become the material of choice.

Additionally, when using electrodes which are placed directly on the heart, it is a requirement that the electrical conductors interconnecting the patch electrode and a signal processing and power generating assembly, be very flexible and resistant to fracture from repeated flexion stresses. As may be appreciated, the heart and the body both undergo continuous movement which cannot be inhibited by the conductors or the electrodes affixed to the surface of the heart. In addition, in recognition of the critical nature of the devices, any fracture or degradation in the electrical performance of the electrode and/or the conductors, is unacceptable.

The electrical characteristics of the design of the conductor element are also critical because of the requirements that the conductor transmit both low voltage sensing signals and high defibrillation currents. Thus, the tip-to-tip resistance and the current capacity properties are as important as the flexure and durability characteristics. Further, it is desirable that the conductors have some degree of redundancy in the event that a failure in a part of the conductor does occur, so that the defibrillator patch will not be rendered inoperative.

The various types of materials for the electrodes and conductors, as well as various specific design considerations, influence the method of affixing the conductors to the wire mesh of the electrode patch. The particular difficulty involves providing secure electrical and mechanical contact between the electrical conductors and the electrode mesh.

SUMMARY OF THE INVENTION

The present invention is directed to the design and construction of a conductor for a defibrillator patch lead or an implantable cardioverter defibrillator. More specifically, the present invention details an improved electrical conductor including a Teflon insulated drawn brazed stranded (DBS) wire cable which is wrapped in a drawn filled tube (DFT) wire multifilar coil and then encased in a biocompatible insulative tubing. The combination of the DBS and DFT wire conductors, which are joined at each end of the lead, lowers the tip-to-tip resistance of the lead, improves the reliability due to the redundancy, and improves corrosion resistance of the DFT wire, and increases the strength and fatigue life of the lead body. The low resistance and the high reliability cannot be achieved by either the DFT conductor or the DBS conductor alone.

BRIEF DESCRIPTION OF THE DRAWINGS

FIG. 2 is an enlarged axial cross-sectional view of a portion of the lead body depicting the conductors.

FIG. 3 is an enlarged cross-sectional view taken along line 3—3 of FIG. 2, depicting the DBS cable.

FIG. 4 is an enlarged cross-sectional view of one DBS wire from the DBS cable.

FIG. 5 is an enlarged cross-sectional view of one of the DFT wires of the lead body.

DETAILED DESCRIPTION OF THE PREFERRED EMBODIMENT

Figure 1:
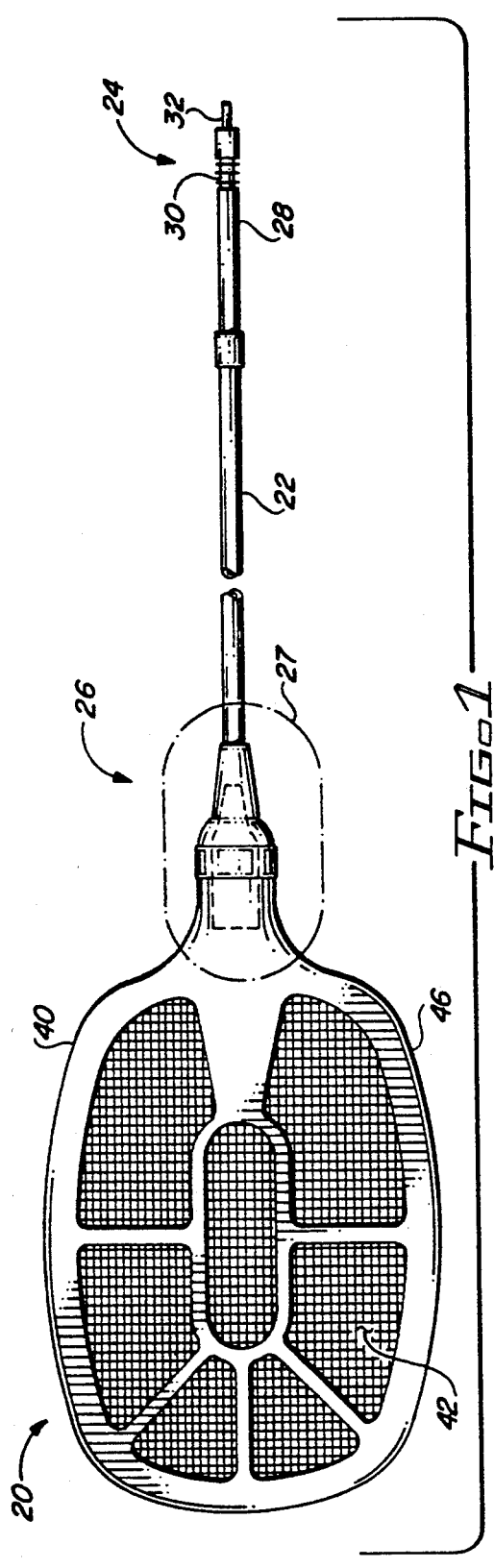
FIG. 1 illustrates a defibrillator patch lead according to the present invention.

FIG. 1 illustrates a defibrillator patch lead 20 including an elongated lead body 22 extending from a proximal end 24 to a distal end 26 according to the present invention. The proximal end 24 includes a connector assembly 28 which includes a biocompatible insulative material formed to provide sealing rings 30, and to leave exposed an electrically conductive connector pin 32. The connector assembly 28 is configured for insertion into a receiving element of a signal processing and pulse generating device (not shown). While the electrode assembly is herein depicted as a defibrillator patch electrode, it should be appreciated that the conductor configuration of the present invention is also applicable to other types of leads and to other devices, such as implantable cardioverter defibrillator accessories including lead adapters or lead extenders.

At the distal end 26 of the lead 20 is located an electrode assembly 40. The electrode assembly 40 includes a wire mesh element 42 which is secured in an area 27 via a conductive connector element 44 (FIG. 6), to the electrical conductors within the elongated lead body 22. The connector element 44 as well as the peripheral edge of the wire mesh element 42 are encased in a molded element 46, which is a biocompatible inert insulation material. The wire mesh element 42 may simply be a round, oval-shaped, or other suitably curved-shape wire mesh preferably formed from 17 to 19 gage (0.003 inch/0.005 inch diameter) titanium or platinum wire.

FIG. 2 is an enlarged axial cross-sectional view of a portion of the lead body 22. Starting at the right side of FIG. 2, the elongated lead body 22 is depicted as including a drawn filled tube (DFT) conductor coil 50 which is wrapped about an insulator 54 which encases a drawn brazed stranded (DBS) conductor cable 52. Preferably, these components are inserted into a biocompatible insulative tubing element 56, such as the insulation material sold under the name Extra Tear Resistant (ETR) Silicone Elastomer tubing, manufactured by Dow Corning, having a wall thickness of approximately 0.6 mm. In this embodiment, the conductor coil 50 includes five helically wound DFT wires 60, described in greater detail below.

FIG. 3 is an enlarged cross-sectional view of the DBS conductor cable 52 taken along cross-sectional line 3—3 of FIG. 2. FIG. 3 illustrates the plurality of individual drawn brazed stranded (DBS) wires 62 which make up the DBS cable 52. The plurality of individual DBS wires 62 are braided together to form the DBS cable 52. In addition, the DBS cable 52 is encased in the insulating material 54, such as the insulation material sold under the name Teflon tape wrap, manufactured by DuPont. FIG. 4 depicts in greater detail a cross-sectional view of one of the DBS wires 62 taken from the DBS cable 52. As depicted in the enlarged view of FIG. 4, the central portion 64 of the DBS wire 62 has a core portion 66 with a plurality of radially extending ridges 68, which combine to form an essentially star-shaped cross-sectional profile. This central portion 64 is preferably a silver matrix conductor. The central portion 64 is encased in an alloy material 70 to form a round wire. The alloy material 70 is preferably a nickel alloy such as MP35N, or may be of a suitable stainless steel or other suitable material. The advantage of the inclusion of material in the star-shaped cross-section for the central portion 64 is exhibited in the form of lower resistance per unit of length.

FIG. 5 depicts an enlarged cross-sectional view of one of the drawn filled tube (DFT) wires 60 which comprise the DFT conductor coil 50. As depicted in FIG. 5, the core of the DFT wire 60 is a solid cylindrical element 72 which is encased in a suitable conductive material 74, such as MP35N. The core of the DFT wire 60 is preferably a silver or copper composition, or some other suitable low resistance material.

Returning to FIG. 2, the DBS cable 52 extends essentially axially within the lead body 22. The individual DBS wires 62 which comprise the DBS cable 52 are braided together in order to provide both strength and flexibility. The DFT conductor coil 50 is wrapped about the DBS cable 52 in an essentially helical manner, providing both structural support and flexibility. The final step in constructing the lead body 22 is installing the DFT conductor coil 50 wrapped DBS cable 52 within the biocompatible insulative tubing material 56, to form the lead body 22 which is lightweight, durable and electrically redundant.

Figure 6:
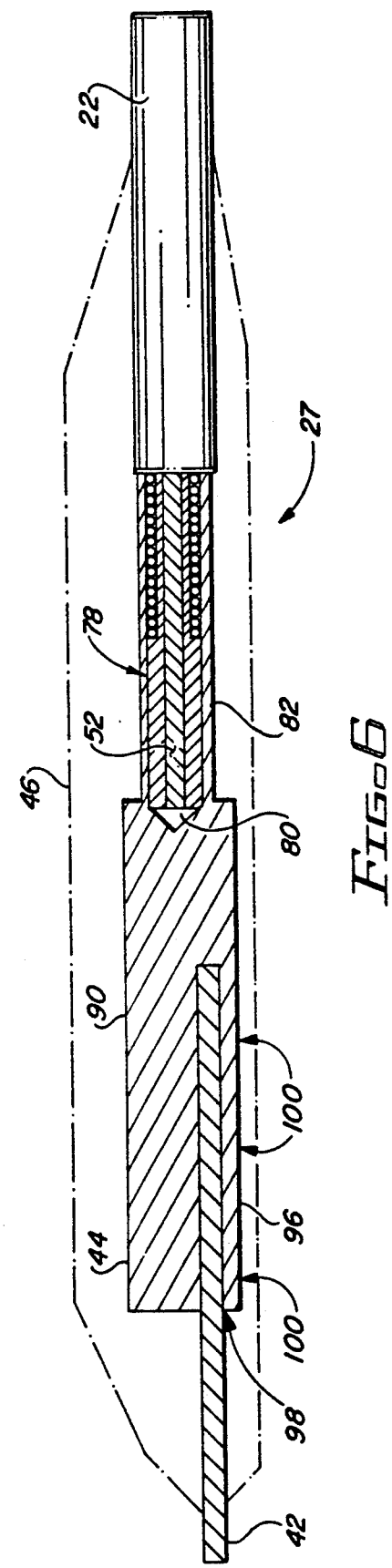
FIG. 6 depicts a cross-sectional view illustrating the conductors of the lead body assembled with the connecting element and wire patch electrode of the present invention.

The area 27 shown in FIG. 1, including the assembled connector element 44 and portions of the elongated lead body 22 and wire mesh element 42, are illustrated in the enlarged cross-sectional view of FIG. 6. For a more complete description of one apparatus and method for providing the interconnection between electrical conductors and the electrode mesh, see Assignee's copending U.S. Pat. application No. 07/926,076, filed Aug. 5, 1992, entitled "IMPLANTABLE DEFIBRILLATOR PATCH LEAD," which is incorporated herein by reference. Briefly, the DBS cable 52 is inserted into a core sleeve 78 and crimped thereto. The core sleeve 78 is configured to be inserted into a hollow cylindrical area 80 defined by a cylindrical element 82 projecting from the connector element 44. Upon insertion of the core sleeve 78, and a portion of the lead body 22, into the cylindrical element 82, the core sleeve 78 is secured within the cylindrical element 82 by crimping or by laser welding.

The connector element 44 also includes a body portion 90 which is preferably formed from titanium or platinum depending on the material for the wire mesh. In FIG. 6, the body portion 90 of connector element 44 includes a retaining flap 96 which defines a slot opening 98 against the body 90. The wire mesh element 42 is inserted into the slot opening 98 and secured via welding to the connector element 44. Preferably, the width of the slot is closely matched to the thickness of the wire mesh element 42. Thus, the thickness of the slot opening 98 is preferably in the range of about 0.25 mm to 0.30 mm.

The connector element 44 is fabricated from titanium or platinum to provide high corrosion resistance and durability. In addition, the wire mesh element 42 is preferably fabricated from titanium, which may have a titanium nitride surface coating, or of platinum or some other suitable material to improve electrical characteristics. As illustrated, the laser weld locations 100 melt the material of the retaining flap 96, securing it to the wire mesh element 42 which is inserted into the slot opening 98. In addition, the material of the wire mesh element 42, as well as the material of the body portion 90 of the connector element 44, have been melted such that the metal of the body 90 is secured to the wire mesh element 42. By this configuration, the interconnection strength between the connecting element 44 and the wire mesh element 42 is significantly enhanced and will survive the repeated flexure accompanying its intended location on the exterior surface of the heart.

It should also be noted that with respect to FIG. 6, substantially all of the connector element 44 and portions of the wire mesh element 42 as well as portions of the elongated lead body 22 will be encased in the biocompatible insulative material of the molded element 46, to provide insulation and to minimize the foreign body reaction to the patch lead 20. The biocompatible coating of the molded element 46 is shown by the dashed lines in FIG. 6.

As an example of the reduction in the tip-to-tip resistance arising from the lead body 22 according to the present invention, the resistance for various cable configurations per unit of length was determined. Using a length of 60 cm as the standard, a DBS cable of a conventional configuration has a resistance of 0.78 Ω, and a DFT coil can have even higher resistance. By comparison, a DBS cable wrapped in a DFT conductor coil according to the present invention has a resistance of 0.56 Ω for the same 60 cm length. Thus, the lead body 22 of the present invention exhibits a 30% reduction in the tip-to-tip electrical resistance.

Although DFT conductors have much higher corrosion resistance than DBS, the DFT coil has relatively high electrical resistance to maintain high fatigue life. In this design, a DFT coil design of very high fatigue life with relatively high electrical resistance is used together with DBS. So the overall design has very low electrical resistance, high fatigue life, and high corrosion resistance.

It should be evident from the foregoing description that the present invention provides many advantages over defibrillator patch leads of the prior art. Although preferred embodiments are specifically illustrated and described herein, it will be appreciated that many modifications and variations of the present invention are possible in light of the above teaching to those skilled in the art. It is preferred, therefore, that the present invention be limited not by the specific disclosure herein, but only by the appended claims.

What is claimed is:

1. An implantable defibrillator patch lead comprising:
   an electrical conductor having a proximal end and a distal end, and at least two different electrically conductive wires extending therebetween, the at least two different wires having dissimilar resistances per unit length;
   an insulating sheath covering the electrical conductor;
   an electrical connector coupled to the proximal end of the electrical conductor;
   a wire mesh patch electrode a the distal end of the electrical conductor; and
   means for affixing the wire mesh patch electrode to the electrical conductor.

2. The implantable defibrillator patch lead of claim 1, wherein the electrical conductor further comprises:
   a cable having a plurality of braided, drawn brazed strand wires;
   an insulator encasing the cable;
   a coil having a plurality of wires wrapped in a helix about the insulator; and
   a biocompatible insulative tube encasing the coil and the cable.

3. The implantable defibrillator patch lead of claim 1, wherein the electrical conductor further comprises:
   a cable having a plurality of braided, drawn brazed strand wires;
   an insulator encasing the cable;
   a coil having a plurality of drawn filled tube wires wrapped in a helix about the insulator; and
   a biocompatible insulative tube encasing the coil and the cable.

4. The implantable defibrillator patch lead of claim 3, wherein the wires of the cable and the wires of the coil are electrically interconnected at their ends.

5. The implantable defibrillator patch lead of claim 3, wherein the electrical conductor has a resistance of less than 10 Ω per 100 cm.

6. The implantable defibrillator patch lead of claim 3, wherein the affixing mans comprises:
   a connector element having a body portion defining a slot into which a portion of the wire mesh patch electrode is inserted and bonded, and a hollow cylindrical portion extending from the body portion of the connector element to receive and securely retain one end of the electrical conductor.

7. The implantable defibrillator patch lead of claim 3, wherein the connector element is formed from a material selected from the group consisting of titanium and platinum, and the wires of the conductor are formed from MP35N and silver.

8. The implantable defibrillator patch lead of claim 3, wherein the connector element is formed from a material selected from the group consisting of titanium and platinum, and the wires of the conductor are formed from stainless steel and silver.

9. An implantable defibrillator patch lead comprising:
   an electrical conductor having an electrically conductive cable wrapped within an electrically conductive coil extending from a proximal end to a distal end;
   an insulating sheath covering the electrical conductor;
   an electrical connector coupled to the proximal end of the electrical conductor;
   a wire mesh patch electrode at the distal end of the electrical conductor; and
   means for affixing the wire mesh patch electrode to the cable and the coil of the electrical conductor.

10. The implantable defibrillator patch lead of claim 9, wherein the cable of the electrical conductor has a plurality of braided, drawn brazed strand wires encased in an insulator, and the coil of the electrical conductor has a plurality of drawn filled tube wires wrapped in a helix about the insulator encasing the cable and a biocompatible insulative tube encasing the coil and the cable.

* * * * *